(12) United States Patent
Tachibana et al.

(10) Patent No.: US 6,585,678 B1
(45) Date of Patent: Jul. 1, 2003

(54) BOOSTER FOR THERAPY OF DISEASE WITH ULTRASOUND AND PHARMACEUTICAL IDLIQU COMPOSITION CONTAINING THE SAME

(75) Inventors: Katsuro Tachibana, Fukuoka (JP); Shunro Tachibana, Fukuoka (JP)

(73) Assignee: Ekos Corporation, Bothell, WA (US)

( * ) Notice: Subject to any disclaimer, the term of this patent is extended or adjusted under 35 U.S.C. 154(b) by 0 days.

(21) Appl. No.: 09/375,339

(22) Filed: Aug. 16, 1999

Related U.S. Application Data

(62) Division of application No. 08/652,690, filed on May 30, 1996, now Pat. No. Re. 36,939.

(30) Foreign Application Priority Data

Mar. 22, 1991 (JP) .............................................. 3-058970

(51) Int. Cl.[7] .............................................. A61B 17/20
(52) U.S. Cl. ....................................................... 604/22
(58) Field of Search ............................ 604/22, 114, 23, 604/24, 26; 600/459, 464, 466, 467, 471

(56) References Cited

U.S. PATENT DOCUMENTS

| | | |
|---|---|---|
| 2,961,382 A | 11/1960 | Singher et al. |
| 4,466,442 A | 8/1984 | Hilmann et al. |
| 4,657,756 A | 4/1987 | Rasor et al. |
| 4,762,915 A | 8/1988 | Kung et al. |

(List continued on next page.)

FOREIGN PATENT DOCUMENTS

| | | |
|---|---|---|
| AU | 634470 | 2/1993 |
| EP | 0 224 934 | 6/1987 |
| EP | 0 278 074 | 8/1988 |
| EP | 0 327 490 | 8/1989 |
| GB | 15 77551 | 10/1980 |
| JP | 52115591 | 9/1977 |
| JP | 02-180275 | 7/1990 |
| WO | WO 89/05159 | 6/1989 |
| WO | WO 89/05160 | 6/1989 |
| WO | WO 90/01971 | 3/1990 |
| WO | WO 80/01365 | 11/1990 |

OTHER PUBLICATIONS

Meltzer et al, J Clin Ultrasound 8(2); 121–7 (Apr. 1980) The Source of Ultrasound Contrast Effect*.
Keller et al, J. Ultrasound Med. 5(9): 493–8 (Sep. 1986) Automated Production and Analysis of Echo Contrast Agents*.
Leong et al, Biomaterials 7: 364–371 (Sep. 1986) Polyanhydrides for Controlled Release of Bioactive Agents*.
B.D. Butler, J Clin. Ultrasound 14(5): 408–12 (Jun. 1986) Production of Microbubbles for Use as Echo Contrast Agents*.
Feinstein et al, J Am. Coll.Cardiol. 3(1): 14–20 (Jan. 1984) Two–dimensional Contrast Echocardiography I. In Vitro Development and Quantitative Analysis of Echo Contrast Agents*.
Lang et al, Circulation 75(1): 229–234 (Jan. 1987) Contrast Ultrasonography of the Kidney: a New Method for Evaluation of Renal Perfusion in Vivo*.

(List continued on next page.)

*Primary Examiner*—Anhtuan T. Nguyen
(74) *Attorney, Agent, or Firm*—Knobbe, Martens, Olson & Bear LLP

(57) ABSTRACT

A booster comprising a plurality of microbubbles of a gas in a liquid, e.g. about $4\times10^7$ cells/ml of microbubbles of a gas having a diameter of 0.1. to 100 μm in a 3 to 5% human serum albumin solution, and a pharmaceutical liquid composition comprising the booster as set forth above and a medicament, which are useful for the therapy of various diseases together with exposure of ultrasonic, where the therapeutic effects of the medicament is enhanced by the application of ultrasound in the presence of the booster.

34 Claims, 2 Drawing Sheets

U.S. PATENT DOCUMENTS

| | | | |
|---|---|---|---|
| 4,774,958 A | | 10/1988 | Feinstein |
| 4,797,285 A | | 1/1989 | Barenholz et al. |
| 4,844,882 A | | 7/1989 | Widder et al. |
| 4,900,540 A | | 2/1990 | Ryan et al. |
| 4,936,281 A | | 6/1990 | Stasz |
| 5,040,537 A | | 8/1991 | Katakura |
| 5,069,664 A | | 12/1991 | Guess et al. |
| 5,088,499 A | | 2/1992 | Unger |
| 5,156,050 A | * | 10/1992 | Schmid et al. ............ 73/628 |
| 5,158,071 A | | 10/1992 | Umemura et al. |
| 5,197,946 A | | 3/1993 | Tachibana |
| 5,209,720 A | | 5/1993 | Unger |
| 5,215,680 A | | 6/1993 | D'Arrigo |
| 5,216,130 A | | 6/1993 | Line et al. |
| 5,269,291 A | * | 12/1993 | Carter .................... 604/22 |
| 5,362,309 A | * | 11/1994 | Carter .................... 604/22 |
| 5,431,663 A | | 7/1995 | Carter |
| 5,836,896 A | * | 11/1998 | Rosenschein ............ 601/2 |
| 5,997,497 A | | 12/1999 | Nita et al. |

OTHER PUBLICATIONS

Vandenburg et al, Am. Heart.J. 115(4): 733–9 (Apr. 1988) Myocardial Risk Area and Peak Gray Level Measurement by Contrast Echocardiography: Effect of Microbubble Size and Concentration, Injection Rate, and Coronary Vasodilation*.

T.F. Kim, Medical News & Perspectives, JAMA 261 (11): 1542 (Mar. 17, 1989) Microbubbles Show Promise for Enhancing Ultrasound Signal, Image, Other Applications*.

C.K. Holland and R.E. Apfel, J. Acoust.Soc.Am. 88(5): 2059–2069 (Nov. 1990) Thresholds for Transient Cavitation Produced by Pulsed Ultrasound in a Controlled Nuclei Environment*.

Wheatley et al, Biomaterials 11(19): 713–7 (Nov. 1990) Contrast Agents for Diagnostic Ultrasound: Development and Evaluation of Polymer–Coated Microbubbles*.

Bleeker et al. J. Ultrasound Med. 9(8): 461–71 (Aug. 1990) On the Application of Ultrasonic Contrast Agents for Blood Flowmetry and Assessment of Cardiac Perfusion*.

* cited by examiner

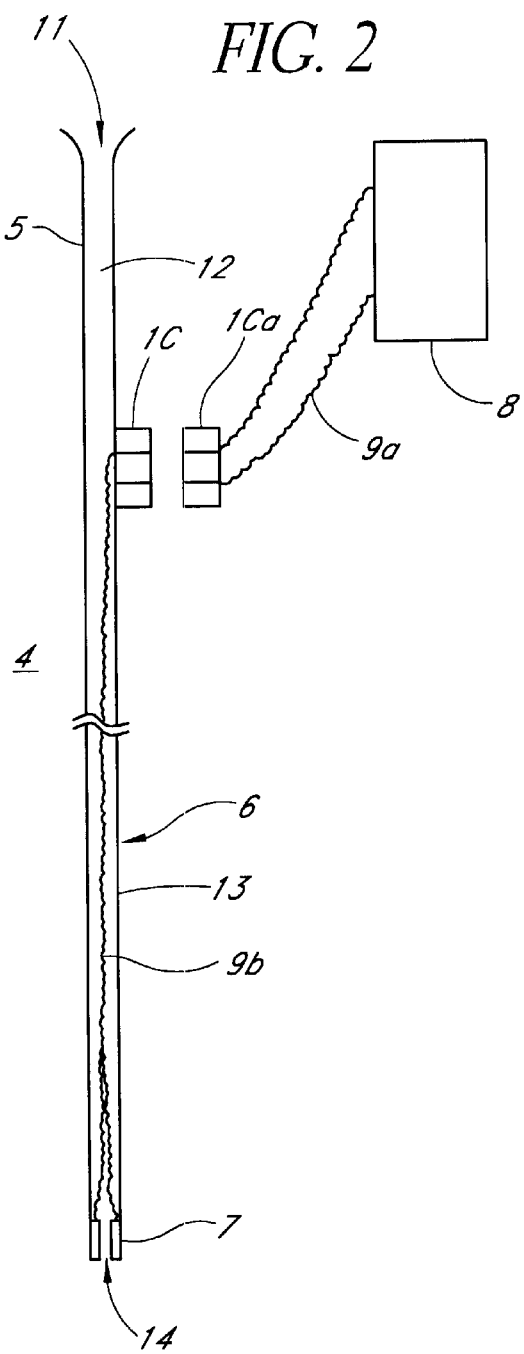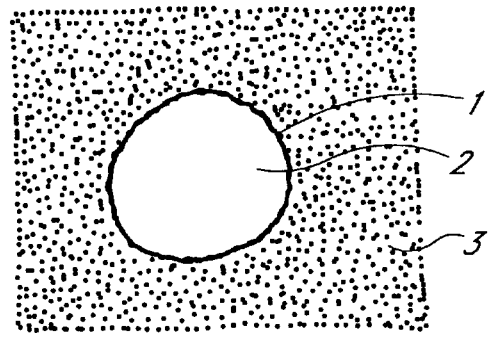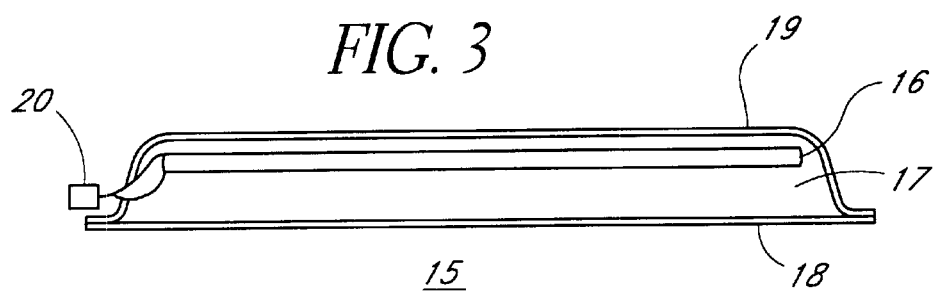

BOOSTER FOR THERAPY OF DISEASE WITH ULTRASOUND AND PHARMACEUTICAL IDLIQU COMPOSITION CONTAINING THE SAME

RELATED APPLICATIONS

This application is a Division of application Ser. No. 08/652,690, filed May 30, 1996, now U.S. Pat. No. RE36,939, which is a reissue of application Ser. No. 07/855,545, now U.S. Pat. No. 5,315,998, filed Mar. 20, 1992 and is incorporated herein by reference in its entirety. This application also claims priority under §119 to Japanese Application No. 3-058970, filed Mar. 22, 1991.

FIELD OF THE INVENTION

This invention relates to a booster useful for enhancing the effects of ultrasound in the therapy of various diseases and a pharmaceutical liquid composition containing the booster and a medicament which shows enhanced diffusion and penetration of the medicament into the body by applying ultrasound. More particularly, it relates to a booster useful for therapy of various disease by applying ultrasound which comprises a plurality of microbubbles of a gas in a liquid, a pharmaceutical liquid composition comprising a plurality of microbubbles of a gas and a medicament in a liquid, and the user thereof in the therapy of various diseases while applying ultrasound.

PRIOR ART

It is known that various diseases are remedied by the aid of ultrasonic vibration. For example, it is described in Japanese Patent First Publication (Kokai) No. 115591/1977, etc. that percutaneous absorption of a medicament is enhanced by applying an ultrasonic vibration. Japanese Patent First Publication (Kokai) No. 180275/1990 discloses a drug-injecting device which is effective on the diffusion and penetration of the drug by applying an ultrasonic vibration in the step of injecting a drug into a human body via a catheter or a drug-injecting tube. U.S. Pat. Nos. 4,953,565 and 5,007,438 also disclose the technique of percutaneous absorption of medicaments by the aid of ultrasonic vibration. It is also reported that a tumor can be remedied by concentratedly applying ultrasound from outside the body.

In order to enhance the therapeutic effects with ultrasound, it is required to apply a high energy ultrasonic vibration. However, ultrasonic vibration at an energy that is too high causes disadvantageously burns or unnecessary heat at the portion other than the desired portion. On the other hand, when the energy of an ultrasonic vibration is lowered for eliminating such disadvantages, there is a problem of less effect of the ultrasound at the desired portion.

SUMMARY OF THE INVENTION

The present inventors have intensively studied enhancing the effects of ultrasound at a lower energy of an ultrasonic vibration and have found that a booster comprising a plurality of microbubbles of a gas in a liquid is useful for the desired enhancement of the effects of ultrasound.

An object of the invention is to provide a booster useful for enhancing the effects of ultrasound which comprises a plurality of microbubbles of a gas in a liquid. Another object of the invention is to provide a pharmaceutical liquid composition containing the booster and a medicament which is useful for the therapy of various diseases together with the application of ultrasound. A further object of the invention is to provide a method for enhancing the effects by the application of ultrasound in the therapy of various diseases which comprises injecting the booster or the pharmaceutical liquid composition as set forth above into the portion to be remedied while applying ultrasound thereto. These and other objects and advantages of the invention will be apparent to those skilled in the art from the following description.

BRIEF DESCRIPTION OF THE DRAWINGS

FIG. 1 shows a schematic view of one of the microbubbles contained in the booster of the invention.

FIG. 2 shows a schematic sectional view of one embodiment of a drug administration device used for injecting, pouring, applying or circulating the booster or the pharmaceutical liquid composition of the invention.

FIG. 3 shows a schematic sectional view of one embodiment of a drug administration device used for transdermal administration of the booster or the pharmaceutical liquid composition of the invention.

DETAILED DESCRIPTION OF THE INVENTION

Figure 4:
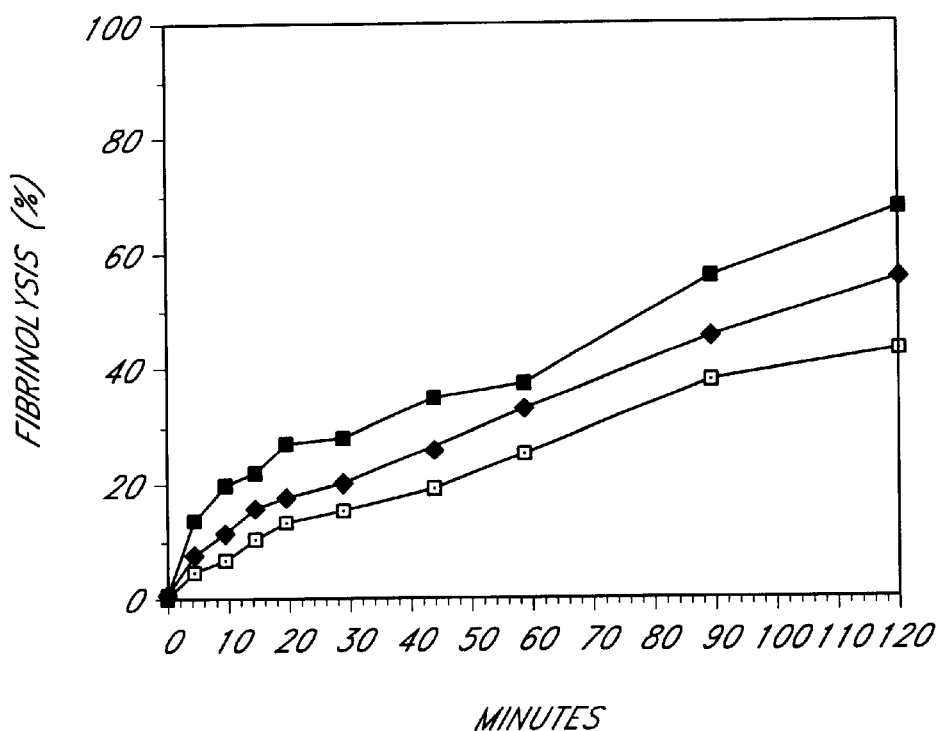
FIG. 4 and FIG. 5 show graphs showing fibrinolysis by application of ultrasound with or without the booster of the invention.

The booster of the invention comprises a liquid containing a plurality of microbubbles of a gas having a diameter of 0.1 to 100 $\mu$m. The microbubbles are formed by entrapping microspheres of a gas into a liquid. The booster contains, for example, about $4 \times 10^7$ of the microbubbles per one milliliter of a liquid. The microbubbles are made of various gases such as air, oxygen gas, carbon dioxide gas, inert gases (e.g. xenon, krypton, argon, neon, helium, etc.), preferably air and oxygen gas. The liquid includes any liquid which can form microbubbles, for example, human serum albumin (e.g. 3 to 5% human serum albumin), a physiological saline solution, a 5% aqueous glucose solution, an aqueous indocyanine green solution, autoblood, an aqueous solution of maglumine diatriazoate (=renografin), and any other X-ray contrast medium.

The booster can be prepared by a known method, for example, by agitating the liquid mentioned above while blowing a gas as mentioned above into the liquid, or alternating exposing the liquid to ultrasound with a sonicator under a gaseous atmosphere, whereby a vibration is applied to the liquid to form microbubbles of the gas.

The pharmaceutical liquid composition of the invention comprises a plurality of microbubbles of a gas and a medicament in a liquid. The microbubbles of a gas and liquid are the same as mentioned above. The medicament includes any known medicaments effective for the desired therapy which can be absorbed percutaneously, for example, anti-thrombosis agents (e.g. urokinase, tissue plasminogen activator, etc.), hormones (e.g. insulin, etc.), theophylline, lidocaine, antibiotics, antineoplastic agents which are sensitive to ultrasound (e.g. doxorublein (=adriamycin), cytarabine (=Ara.C), etc.), and the like. The medicament can be contained in a therapeutically effective amount as usually used. The pharmaceutical liquid composition can be prepared by mixing a medicament with a booster comprising a plurality of microbubbles of a gas in a liquid. The mixing ratio may vary depending on the desired amount and kind of the medicament and the kind of the liquid, but is usually in a range of 1:100 to 100:1 by weight (a medicament/a booster).

According to the invention, the therapeutic effect of ultrasound is boosted by the presence of a booster of the invention. Particularly, when a pharmaceutical liquid composition containing the booster and a medicament is poured or injected into a body in parenteral routes, such as intravenously, percutaneously or intramuscularly, while applying thereto an ultrasonic vibration, the therapeutic effects of the medicament is significantly enhanced. When an ultrasound from an ultrasonic element is applied to the liquid containing the booster and medicament, cavitation occurs in the liquid composition, and the medicament is diffused and penetrated into the desired portion of the biobody by the aid of vibration induced by the cavitation. The cavitation occurs when the level of vibration energy exceeds a certain threshold value. When the ultrasound is applied to the liquid composition of the invention, the threshold value of the vibration energy is reduced due to the presence of a plurality of microbubbles of a gas. That is, the microbubbles of a gas act as nucleus, of cavitation and thereby the cavitation occurs more easily. Therefore, according to the invention, the desired ultrasonic energy necessary for the desired diffusion and penetration of a medicament is reduced.

The desired ultrasound is applied by conventional ultrasonic devices which can supply an ultrasonic signal of 20 KHz to several MHz.

With reference to the accompanying drawings, the invention is illustrated in more detail.

FIG. 1 shows a schematic view of one of the plurality of microbubbles of a gas contained in the booster of the invention, wherein the microbubble of a gas has a diameter of 0.1 to 100 $\mu$m and is composed of a shell of human serum albumin 1 and gas 2 entrapped within the microbubble. The microbubbles are contained in a liquid 3 such as 5% human serum albumin solution in an amount of, for example, above $4 \times 10^7$ cells/ml.

The booster is mixed with a medicament to give a pharmaceutical liquid composition. The pharmaceutical liquid composition is directly administered to the diseased part with an appropriate device, for example, with a drug administration device 4 as shown in FIG. 2. The drug administration device 4 comprises a base tube 5 to which the pharmaceutical liquid composition is supplied, and an end tube 6 which is to be inserted into the tissue of the biobody and through which the pharmaceutical liquid composition is poured or injected into the disease part. The end tube 6 is provided with an ultrasonic element 7 (e.g. a cylindrical ceramic oscillator, etc.). The ultrasonic element 7 is supplied by an ultrasonic signal of 20 KHz to several MHz from an ultrasonic oscillation circuit 8 via a conductor 9a, connectors 10a and 10b provided on the side of the base tube 5, a part of the base tube 5 and a conductor 9b provided within the end tube 6.

The application or injection of a medicament is carried out in the form of a pharmaceutical liquid composition which is prepared by previously mixing the medicament with the booster comprising a plurality of microbubbles of a gas in a liquid, wherein the medicament and the booster are mixed in a ration of 1:100 to 100:1 by weight. The pharmaceutical liquid composition is poured into the base tube 5 from the supply opening 11 provided on the tip of the base tube 5, passes through a flow path 12 within the base tube 5 and a flow path 13 within the end tube 6 and is then administered to the diseased part or the portion close thereto of the patient via a pouring opening 14 provided at the bottom of the end tube 6.

When the pharmaceutical liquid composition is administered into the diseased part or the portion close thereto through the pouring opening 14, an ultrasonic energy generated from an ultrasonic element 7 is applied to the liquid composition, by which cavitation occurs due to the ultrasonic energy. Microbubbles are formed at the occurrence of cavitation and when the microbubbles are decomposed, energy is generated, by which diffusion and penetration of the medicament is promoted. Since the pharmaceutical liquid composition contains a plurality of microbubbles of a gas, the microbubbles act as a nucleus for the cavitation by which the cavitation occurs more easily, in other words, the threshold value of occurrence of cavitation lowers. Accordingly, it is possible to generate the cavitation with less energy than the case of using no booster.

When an ultrasonic vibration is applied to a liquid, if the liquid contains any material being able to become a nucleus, the cavitation occurs generally at a lower threshold value of energy, but it has been found that the cavitation occurs most easily where the liquid contains microbubbles of a gas having a diameter of 0.1 to 100 $\mu$m.

The drug administration device 4 as shown in FIG. 2 can be used, for example, for administering a pharmaceutical liquid composition into a blood vessel. For instance, in the treatment of coronary thrombosis, a pharmaceutical liquid composition comprising a booster of the invention and a urokinase is injected into the part of thrombosis or the close portion thereof with the drug administration device 4 where the tip of the end tube 6 is inserted into the portion close to the thrombosis with applying ultrasound, by which the thrombolytic effects of the medicament are significantly increased and further the blood flow is recovered within a shorter period of time in comparison with the administration of the medicament without the booster. The drug administration device 4 may also be used for the removing hematoma in bleeding of brain. For example, a pharmaceutical liquid composition comprising a booster of the invention and a thrombolytic agent (e.g. urokinase) is administered to the portion of hematoma with the drug administration device 4 with applying ultrasound like the above, by which the hematoma is easily lysed.

In another embodiment of the invention, the pharmaceutical liquid composition can be administered transdermally with a drug administration device 15 as shown in FIG. 3.

In the drug administration device 15 suitable for transdermal administration of a medicament, a layer of a medicament 17 is provided below an ultrasonic element 16 (e.g. a disc shaped ceramic oscillator, etc.), under which an adhesive layer 18 having a medicament permeability is laminated, the whole of which is covered with a plastic cover 19. The ultrasonic element 16 is supplied by ultrasonic signal from an ultrasonic oscillation circuit provided outside via a connector 20, as shown in the drug administration device 4 in FIG. 2.

In the device 15 of FIG. 3, a pharmaceutical liquid composition comprising a mixture of a booster and a medicament is contained in the layer of a medicament 17. When this device 15 is used, it is adhered onto the skin with facing the adhesive layer 18 to the skin, and then an ultrasonic signal is supplied to the ultrasonic element 16, by which an ultrasonic vibration from the ultrasonic element 16 is given to both of the medicament layer 17 and the skin and thereby the medicament contained in the medicament layer 17 is passed through the skin and is penetrated into the tissue to be treated. In this embodiment, since microbubbles of a gas are contained in the medicament layer 17, cavitation occurs easily within the medicament layer 17 by application of ultrasound, and hence even when lower energy of the ultrasonic vibration is supplied from the ultrasonic element 16, the diffusion and penetration of the medicament can effectively be done to result in rapid absorption of the medicament.

The booster of the invention may also be used alone without mixing with a medicament in the therapy with ultrasound. For example, in the therapy of tumors by heating the diseased part of the tissue with ultrasound, that is, by concentratedly applying an ultrasonic vibration outside the biobody, a booster comprising a plurality of microbubbles of a gas in a liquid of the invention is previously injected into the blood vessel or to the portion close to the diseased part before application of ultrasound, by which the effect of heating with ultrasound is enhanced and thereby the therapeutic effects are significantly improved. In this embodiment, cavitation occurs also by the ultrasonic vibration more easily because of using a liquid containing microbubbles of a gas, and hence, even by less energy of the ultrasonic vibration supplied from the ultrasonic element, the ultrasonic energy sufficient to the therapy is obtained and thereby the undesirable burns and unnecessary heating at other portions can be avoided.

In the treatment of tumors, it is, of course, more effective to use it together with a chemotherapeutic agent suitable for the treatment of the tumors, by which the effects of the chemotherapeutic agent are more enhanced, where the diffusion and penetration of the medicament are improved owing to the booster.

The substance such as human serum albumin in the booster of the invention is easily metabolized within the biobody and excreted outside the biobody, and hence, it is not harmful to human body. Besides, the amount of gas trapped within the microbubbles is extremely small and is easily dissolved in the blood fluid. Accordingly, the booster of the invention has no problem in the safety thereof.

The preparation of the booster and pharmaceutical liquid composition of the invention and effects thereof are illustrated by the following Examples and Experiment, but it should not be construed to be limited thereto.

EXAMPLE 1

Preparation of a Booster

A 5% human serum albumin (8 ml) in a 10 ml-volume syringe is exposed to ultrasound with a sonicator (frequency, 20 KHz) by which vibration is given to the human serum albumin and a plurality of microbubbles of air are formed in the human serum albumin to give a booster comprising a human serum albumin containing a plurality of microbubbles of air.

EXAMPLE 2

Preparation of a Pharmaceutical Liquid Composition

The 5% human serum albumin containing a plurality of microbubbles of air prepared in Example 1 is mixed with urokinase (concentration 1200 IU/ml) to give the desired pharmaceutical liquid composition.

Experiment

1. Forming Artificial Thrombosis

An artificial thrombosis was formed by Chandler's method. Blood (1 ml) that was collected from healthy humans (two persons) was entered into a flexible tube (inside diameter 3 mm, length 265 mm) and thereto was added calcium chloride, and then the tube was made a loop like shape, which was rotated at 12 rpm for 20 minutes to give an artificial thrombosis model.

2. Ultrasonic Catheter

A ceramic ultrasonic element (width 2 mm, length 5 mm, thickness 1 mm) was inserted into the tip of a catheter (diameter 2 mm), and an oscillating element was connected to an oscillator provided outside with a fine connector passed through the catheter. A fine tube for pouring a test solution was provided at an opening opposite to the opening of the catheter end.

3. Test Method

The artificial thrombosis prepared above was added to a test tube together with blood, and the ultrasonic catheter was inserted into the test tube so that the end of the catheter was set close to the portion of the artificial thrombosis (at a distance of about 5 mm), and to the test tube a mixture of urokinase and a booster prepared in Example 1 was added at a rate of 1 ml per minute, wherein urokinase (concentration 1200 IU/ml) and the booster were mixed immediately before pouring at a mixing ration of 1:1 by weight. The mixture was refluxed while keeping the volume of the test solution at a constant level by removing excess volume of the solution by suction. The ultrasound (170 KHz) was exposed to the mixture by a pulse method (exposed for 2 seconds and stopped for 4 seconds) for 2 minutes (total exposing time 40 seconds). After the exposure, the ultrasonic catheter was removed from the test tube, and the mixture was incubated at 37 degrees C. for 5 to 120 minutes, washed with a physiological saline solution several times and dried overnight. Thereafter, the dried mixture was weighed. As a control, the above was repeated by using only a physiological saline solution.

4. Test Results $$\text{Fibrinolysis rate (\%)} = \frac{\begin{bmatrix}\text{Weight of}\\\text{thrombosis}\\\text{in control}\end{bmatrix} - \begin{bmatrix}\text{Weight of}\\\text{thrombosis}\\\text{treated}\end{bmatrix}}{\text{Weight of thrombosis in control}} \times 100$$

Figure 5:
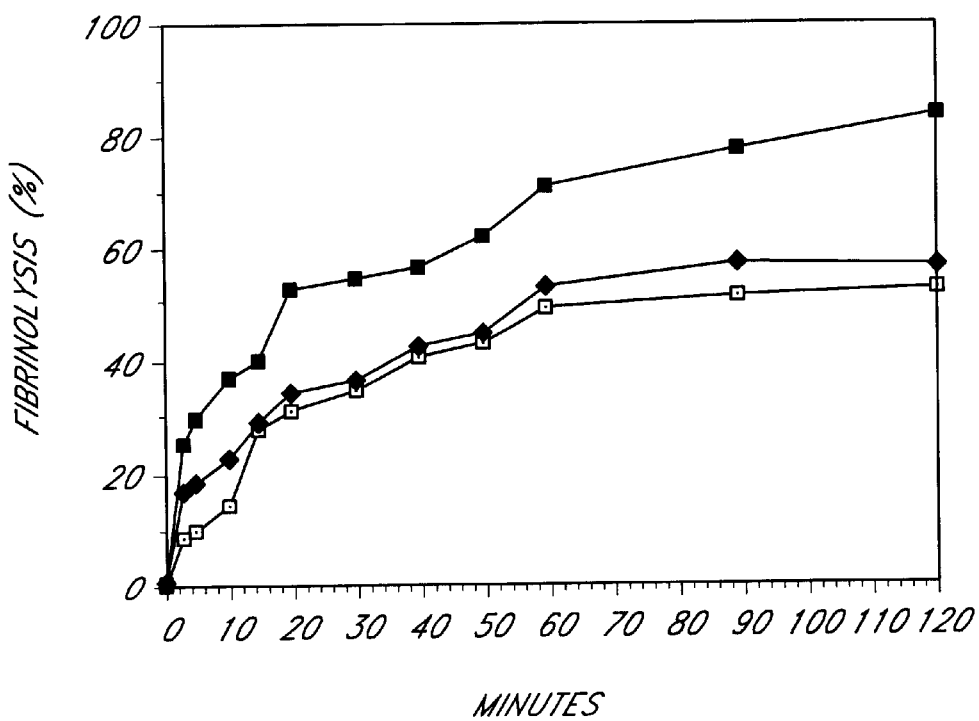

The results are shown in the accompanying FIGS. 4 and 5 wherein there are shown in average of twice tests.

FIG. 4 shows the results in the thrombosis prepared by using blood collected from one person, wherein the symbol —□— is the data obtained in the addition of urokinase alone without exposure of ultrasound, —♦— is the data obtained in the addition of urokinase alone with exposure of ultrasound, and —■— is the data obtained in the addition of a mixture of urokinase and the booster with exposure of ultrasound.

As shown in FIG. 4, the time for achieving 20% fibrinolysis was 45 minutes by urokinase alone without exposure of ultrasound, 30 minutes by a combination of urokinase and exposure of ultrasound, and only 10 minutes by a combination of a mixture of urokinase and a booster and exposure of ultrasound. The fibrinolytic effects of urokinase (both the rate of fibrinolysis and the fibrinolytic time) were significantly enhanced by using a booster with application of ultrasound.

FIG. 5 shows the results in the thrombosis prepared by using blood collected from another person and with reduced energy of ultrasound by 15%, wherein the symbols are the same as in FIG. 4. As shown in FIG. 5, the fibrinolytic effects were significantly enhanced by using a mixture of urokinase and the booster. That is, in case of using urokinase alone with exposure of ultrasound, the 50% fibrinolysis was achieved by the treatment for 60 minutes, but in case of using a mixture of urokinase and the booster with exposure of ultrasound, it reduced to one fourth, i.e. it was achieved by the treatment only for 15 minutes.

What is claimed is:

1. A catheter, comprising:
   a flexible elongated member including a lumen, a lumen delivery port, and a distal portion, the elongated member being adapted for intravascular positioning; and
   an ultrasonic transducer coupled to the distal portion of the elongated member and generating ultrasound energy, and wherein the lumen is acoustically isolated from the ultrasound energy to permit delivery of microbubbles to a selected tissue site from the lumen delivery port.

2. The catheter of claim 1, wherein the lumen is acoustically isolated from the ultrasound energy to permit the delivery of the microbubbles with a medicament to the selected tissue site.

3. The catheter of claim 1, wherein the lumen is sufficiently acoustically insulated from the ultrasound energy to permit the delivery of the microbubbles with a medicament to the selected tissue site.

4. The catheter of claim 1, wherein the ultrasound transducer is positioned a sufficient distance from the lumen to acoustically isolate the lumen from the ultrasound energy.

5. A drug administration device for enhancing delivery of a liquid drug solution to a treatment site within a body, comprising:
   an elongated member having a proximal end portion and a distal end portion and formed with a drug delivery lumen extending longitudinally therethrough, said distal end portion of said elongated member being formed for insertion into said treatment site within said body; and
   an ultrasonic element disposed on said distal end portion of said elongated member, said ultrasonic element being adapted to direct ultrasound energy into said drug solution for producing cavitation in said drug solution.

6. The drug administration device of claim 5, wherein said proximal end portion of said elongated member comprises a base tube and said distal end portion of said elongated member comprises an end tube.

7. The drug administration device of claim 5 wherein said distal end portion of said elongated member is formed for insertion through a blood vessel.

8. The drug administration device of claim 5 wherein said elongated member is flexible.

9. The drug administration device of claim 5 wherein said drug solution contains a plurality of microbubbles of a gas and at least a portion of said lumen is acoustically isolated from said ultrasonic element such that said microbubbles are substantially unaffected by said ultrasound energy while in said lumen.

10. The drug administration device of claim 5 wherein said ultrasonic element is a cylindrical ceramic oscillator.

11. A drug administration device for enhancing delivery of a liquid drug solution to a treatment site within a body, said drug solution containing a plurality of microbubbles of a gas, comprising:
    a flexible elongated member having a proximal end portion and a distal end portion and formed with a drug delivery lumen extending longitudinally therethrough, said distal end portion of said elongated member being adapted for insertion into a blood vessel within said body; and
    an ultrasonic element disposed on said distal end portion of said elongated member, said ultrasonic element being adapted to direct ultrasound energy into said drug solution for producing cavitation in said drug solution, at least a portion of said lumen being acoustically isolated from said ultrasonic element.

12. A drug administration system, comprising:
    an elongated member having a proximal end portion and a distal end portion and formed with a drug delivery lumen extending longitudinally therethrough, said distal end portion of said elongated member being formed for insertion into a treatment site within a body;
    a liquid drug solution for treating tissue at said treatment site; and
    an ultrasonic element disposed on said distal end portion of said elongated member, said ultrasonic element being adapted to direct ultrasound energy into said drug solution for producing cavitation in said drug solution, wherein said cavitation enhances absorption of said drug solution into said tissue.

13. The drug administration system of claim 12, wherein said liquid drug solution further comprises a plurality of microbubbles of a gas for enhancing said cavitation.

14. A drug administration device for enhancing transdermal administration of a medicament, comprising:
    a transfer member having a top surface and a bottom surface, said bottom surface being adapted for contact with a portion of a patient's skin, said transfer member being permeable to said medicament;
    a cover located over said top surface and forming a chamber between said cover and said top surface,
    a selected quantity of said medicament located within said chamber; and
    an ultrasonic element located within said chamber for transmitting ultrasonic energy to said medicament and said skin for enhancing delivery of said medicament across said transfer member into said skin.

15. The drug administration device of claim 14 wherein said ultrasonic element is adapted to produce cavitation in said medicament.

16. The drug administration device of claim 15 wherein said medicament includes a plurality of microbubbles of a gas for enhancing said cavitation in said medicament.

17. The drug administration device of claim 14 wherein said ultrasonic element is a disc shaped ceramic oscillator.

18. A system for treating a selected tissue site with ultrasound energy, comprising:
    an elongated member having a proximal end portion and a distal end portion and formed with a delivery lumen extending longitudinally therethrough, said distal end portion of said elongated member being formed for advancement to said tissue site;
    a liquid composition for delivery through said delivery lumen to said tissue site;
    a plurality of microbubbles of a gas contained within said liquid composition; and
    an ultrasonic element disposed on said distal end portion, said ultrasonic element being adapted to direct said ultrasound energy into said liquid composition wherein said microbubbles enhance an effect of said ultrasound energy at said tissue site.

19. The system of claim 18, wherein said microbubbles enhance said effect of said ultrasound energy by reducing an energy level of said ultrasound energy required for producing cavitation in said liquid composition.

20. The system of claim 18, wherein said liquid composition comprises a medicament and said ultrasound energy enhances delivery of said medicament to said tissue site by diffusing said medicament and increasing penetration of said medicament at said tissue site.

21. The system of claim 20, wherein said medicament comprises an anti-thrombosis agent.

22. The system of claim 20, wherein said medicament comprises an antibiotic.

23. The system of claim 20, wherein said medicament comprises a chemotherapeutic agent.

24. The system of claim 18, wherein at least some of said microbubbles have a diameter of about 0.1 to 100 micrometers.

25. The system of claim 18, wherein said liquid composition comprises a human serum albumin solution.

26. The system of claim 18, wherein said liquid composition comprises a saline solution.

27. The system of claim 18, wherein at least some of said microbubbles have a shell comprising a human serum albumin solution.

28. The system of claim 18, wherein said ultrasound energy is produced at a frequency of about 20 kHz to 3.0 MHz.

29. The device of claim 18 further comprising a pharmaceutical agent in which said agent is a thrombolytic agent.

30. The device of claim 18 further comprising a pharmaceutical agent in which said agent is a chemotherapeutic agent.

31. A drug administration device for dissolving a thrombus, comprising:
   an anti-thrombosis agent; and
   a base tube containing:
      a first opening for receiving the anti-thrombosis agent;
      a second opening for delivering the anti-thrombosis agent into a patient; and
      an ultrasound element adjacent to the second opening vibrating at about 20 kHz to about several MHz and capable of coupling vibrational energy into the anti-thrombosis agent.

32. A drug administration device for internal administration of a pharmaceutical liquid comprising:
   a base tube containing:
      a first opening for receiving the pharmaceutical liquid;
      a second opening for delivering the pharmaceutical liquid into a patient; and
      an ultrasound element adjacent to the second opening capable of coupling vibrational energy into the pharmaceutical liquid to a level sufficient to cause cavitation in the pharmaceutical liquid.

33. A method of dissolving a thrombus, comprising:
   providing an anti-thrombosis agent;
   providing a drug administration device containing:
      a base tube having first and second openings at opposite ends thereof; and
      an ultrasound transducer disposed in an area adjacent to the second opening;
   vibrating the ultrasound element at about 20 kHz to about several MHz;
   introducing the anti-thrombosis agent into the first opening; and
   allowing the anti-thrombosis agent to exit the second opening.

34. A method of administering a pharmaceutical liquid, comprising:
   providing a drug administration device containing:
      a base tube having first and second openings at opposite ends thereof; and
      an ultrasonic transducer disposed in an area adjacent to the second opening;
   introducing the pharmaceutical liquid into the first opening;
   allowing the pharmaceutical liquid to exit the second opening; and
   vibrating the ultrasound element at a low energy level sufficient to cause cavitation in said liquid.

* * * * *

UNITED STATES PATENT AND TRADEMARK OFFICE
CERTIFICATE OF CORRECTION

PATENT NO.   : 6,585,678 B1
DATED        : July 1, 2003
INVENTOR(S)  : Katsuro Tachibana and Shunro Tachibana It is certified that error appears in the above-identified patent and that said Letters Patent is hereby corrected as shown below:

<u>Title page, Item [54] and Column 1, line 3,</u>
Should read -- BOOSTER FOR THERAPY OF DISEASE WITH ULTRASOUND AND PHARMACEUTICAL LIQUID COMPOSITION CONTAINING THE SAME --

Item [62], Related U.S. Application Data, should read -- Division of application No. 08/652,690, filed on May 30, 1996, now Pat. No. Re. 36,939, which is a reissue of application No. 07/855,545, now U.S. Pat. No. 5,315,998, filed March 20, 1992. --

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,585,678 B1
DATED : July 1, 2003
INVENTOR(S) : Katsuro Tachibana and Shunro Tachibana It is certified that error appears in the above-identified patent and that said Letters Patent is hereby corrected as shown below:

<u>Title page,</u>
Item [73], Assignee, "Ekos Corporation, Bothell, WA (US)" is incorrect. No assignment has been made, and there is no assignee.

Signed and Sealed this

Sixteenth Day of March, 2004

JON W. DUDAS
*Acting Director of the United States Patent and Trademark Office*